US00PP18644P3

(12) United States Plant Patent

Van Dijk

(10) Patent No.: US PP18,644 P3

(45) Date of Patent: Mar. 25, 2008

(54) *ANTHURIUM* PLANT NAMED 'ANTHEPEDI'

(50) Latin Name: ***Anthurium andreanum* L.**
Varietal Denomination: Anthepedi

(75) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 11/482,613

(22) Filed: Jul. 7, 2006

(65) Prior Publication Data

US 2008/0010713 P1 Jan. 10, 2008

(51) Int. Cl.
*A01H 5/00* (2006.01)

(52) U.S. Cl. ..... Plt./365

(58) Field of Classification Search ..... Plt./365, Plt./369, 367
See application file for complete search history.

(56) References Cited

PUBLICATIONS

GTITM UPOVROM Citation for 'Anthepedi' as per PBR QZ PBR 20040460; Mar. 11, 2004.*

* cited by examiner

*Primary Examiner*—Kent Bell
(74) *Attorney, Agent, or Firm*—Jondle & Associates, P.C.

(57) ABSTRACT

A new *Anthurium* plant particularly distinguished by red, durable spathes that slowly turn brown with age, dark-green, compact, durable leaves, medium-long erect peduncle, more inflorescences than leaves, rich shoot formation, flowers early and freely throughout the year, a compact and full plant habit with a plant height around 30 cm, is disclosed.

1 Drawing Sheet

Genus and species: *Anthurium andreanum* L.
Variety denomination: 'Anthepedi'.

BACKGROUND OF THE NEW PLANT

The present invention comprises a new and distinct cultivar of *Anthurium,* botanically known as *Anthurium andreanum* L., and hereinafter referred to by the cultivar name 'Anthepedi'. The new cultivar originated from a hybridization made in 1997 in Bleiswijk, The Netherlands. The female parent was the proprietary pink-color *Anthurium* pot plant '95-634-01' (unpatented), while the male parent was an unidentified *Anthurium* plant (unpatented).

The new cultivar was selected in 1999 from the results of the hybridization and has been asexually reproduced repeatedly by tissue culture in Bleiswijk, The Netherlands over a six-year period. The present invention has been found to retain its distinctive characteristics through successive asexual propagations.

Plant Breeder's Rights for this cultivar were applied with the European Union on Mar. 11, 2004 and in Japan on Apr. 30, 2004.

SUMMARY OF THE INVENTION

The following are the most outstanding and distinguishing characteristics of this new cultivar when grown under normal horticultural practices in Bleiswijk, The Netherlands.

1) Red, durable spathes;
2) Dark-green leaves that are compact and durable;
3) Medium long erect peduncle which holds the inflorescences just above the foliage;
4) Excellent leaf to inflorescence ratio;
5) Rich shoot formation;
6) Compact and full plant habit;

7) Flowers early and rich and is freely flowering throughout the year; and
8) Is a type of potplant with a plant height around 30 cm.

DESCRIPTION OF PHOTOGRAPH

This new *Anthurium* plant is illustrated by the accompanying photograph which shows the overall plant habit including blooms, buds and foliage of the plant; the colors shown are as true as can be reasonably obtained by conventional photographic procedures. The photograph is of a 56-week old plant grown in a greenhouse in Bleiswijk, The Netherlands.

DESCRIPTION OF THE NEW CULTIVAR

The following detailed description sets forth the distinctive characteristics of 'Anthepedi'. The data which define these characteristics were collected from asexual reproductions carried out in Bleiswijk, The Netherlands. The plant history was taken on 56-week old plants which were planted from tissue culture in 14-cm pots and grown in a glass greenhouse between 19° C. and 24° C. Observations were made in May of 2006. Color readings were taken under 5000 lux natural light in the greenhouse. Color references are primarily to the R.H.S. Colour Chart of The Royal Horticultural Society of London (RHS) (2001).

DETAILED BOTANICAL DESCRIPTION

Classification:
*Family.*—Aracea.
*Botanical.*—*Anthurium andreanum* L.
*Common.*—*Anthurium.*

Parentage:
*Female parent.*—'95-634-01', a proprietary pink-flowered *Anthurium* plant (unpatented).
*Male parent.*—An unidentified *Anthurium* plant (unpatented).

Propagation:

*Propagation.*—Tissue culture.

*Root description.*—Fleshy-pink to light-brown roots with smaller hairy lateral roots; root-tips are yellow.

*Time to produce a finished flowering plant.*—55–60 weeks for a 14 cm pot.

Plant:

*Growth habit.*—Herbaceous perennial.

*Height (measured from soil, including inflorescence).*—30 cm.

*Width (measured from leaf tips).*—30 cm to 35 cm.

Leaves:

*Immature leaves.*—Length: 4.0 cm. Width: 2.5 cm. Color (upper surface): RHS 146A (green). Texture: Very shiny.

*Male leaves.*—Length (fully expanded): 17 cm to 20 cm. Width: 11 cm to 13 cm. Shape: Elliptical-cordate, weakly cupped. Apex: Acuminate. Base: Cordate. Leaf Margin: Entire. Leaf blade angle with the petiole: Between 110 degrees and 150 degrees. Color: Upper surface: RHS 139A (green). Lower surface: RHS 137B (light-green). Texture: Shiny, leathery and thick. Venation: The mid-vein and primary veins (the veins which radiate out from junction of petiole and leaf) protrude at the underside of the leaf blade. Venation color: Upper surface: RHS 137C (green). Lower surface: RHS 146D.

*Lobes.*—Arrangement: Leaf blade has two small lobes extending past the petiole. Length of lobes of mature leaf blades: 17 cm. Width of lobes of mature leaf blade: 10 cm. Distance for petiole/leaf junction to highest point on lobes of mature leaf blades: 3.5 cm to 4.5 cm.

*Petiole.*—Cross-section: Round. Diameter: 0.2 cm to 0.3 cm. Length (for mature leaf): 20 cm. Color: Mature leaf: RHS 137B. Immature leaf: RHS 164A. Cataphyl color surrounding the petiole: RHS 144B (light-green) with a bit of RHS 179A (reddish) at the tip.

Inflorescence:

*Arrangement.*—Single.

*Flowering habit (length of flowering season).*—Continuous.

*Number of inflorescences per plant.*—4 to 10.

*Fragrance.*—Absent.

Spathe:

*Buds.*—The spathe is tightly rolled around the spadix and extrudes from the peduncle sheath. After the spathe is fully opened the peduncle elongates some extra centimeters.

*Arrangement.*—Spathe angle with the peduncle is between 80 degrees and 100 degrees; the spathe stands on a slightly curved wiry peduncle about 5 cm to 10 cm above the foliage.

*Shape.*—Ovate, fully-opened is cupped.

*Apex.*—Mucronate tip.

*Base.*—Cordate.

*Margin.*—Entire.

*Size.*—Height: 30 cm. Length: 7 cm to 9 cm. Width: 9 cm to 10 cm.

*Color.*—Just fully open: Upper surface: RHS 53B (red). Lower surface: RHS 53C (red). 7 to 8 weeks after opening: RHS 185A (brownish-red). 14 to 16 months after opening: Complete spathe dies. Edge of lobes of spathe (time of year can determine whether the edges of lobes will be green or not); Upper surface: RHS 144A (light-green). Lower surface: RHS 146D (green).

Peduncle:

*Shape.*—Erect.

*Cross-section.*—Round.

*Length.*—20 cm to 25 cm.

*Diameter.*—0.3 cm to 0.4 cm.

Flowering time: One small untreated tissue culture plant of 2 cm tall will flower, depending on season. After 15 to 16 months, 2 to 3 blossoms appear. More blossoms appear after some additional weeks so that a full flowering and salable plant will have 4 to 10 red spathes. Smaller blossoms may occur on less mature growth.

Spadix:

*Size.*—Height: 2.5 cm to 4 cm. Length: 4 cm. Width (at apex): 0.5 cm to 0.7 cm. Diameter (at base): 0.6 cm to 0.8 cm.

*Shape.*—Columnar.

*Color.*—Immature: RHS 153D (green-yellow). Mature: RHS 155B (white). Ages to: RHS 141A (green).

Flowers:

*Quantity per spadix.*—200 to 300.

*Shape.*—Rounded.

*Size.*—Length: 0.1 cm to 0.2 cm. Diameter (max): 0.2 cm.

*Color.*—RHS 155B (white).

Reproductive organs:

*Stamens.*—Not visible.

*Pollen.*—Sparse.

*Pollen color.*—RHS 156D (white).

*Pistil.*—Quantity: Sparse. Length: Less than 0.01 cm. Color: RHS 156D.

*Style.*—Not observed.

*Stigma.*—Shape: Ovoid. Diameter: Less than 0.01 cm. Color: RHS 155D (white).

*Ovary.*—Rarely visible.

*Ovary color.*—RHS 155D (white).

Fruit and seed set: Seed production has not been observed to date.

Disease and insect resistance: No particular resistance or susceptibility different from other *Anthurium* varieties.

COMPARISON WITH PARENTAL AND COMMERCIAL CULTIVARS

'Anthepedi' differs from the female parent '95-634-01' (unpatented), by having larger, red spathes, while '95-634-01' has smaller, pink spathes. In addition, 'Anthepedi' has a less compact plant habit than '95-634-01'.

A comparison with the male parent, an unknown *Anthurium* plant, (unpatented), is not possible because detailed information is unknown.

'Anthepedi' is similar to the commercial variety 'Anthbnena' (U.S. Plant Pat. No. 15,199) however, there are differences as listed in Table 1 below:

TABLE 1

Comparison of characteristics between 'Anthepedi' and 'Anthbnena'

| Characteristic | 'Anthepedi' | 'Anthbnena' |
|---|---|---|
| Leaf length | 17.0 cm to 20.0 cm | 16.0 cm |
| Leaf width | 11.0 cm to 13.0 cm | 10.0 cm |
| Spathe length | 7.0 cm to 9.0 cm | 7.0 cm |
| Spathe width | 9.0 cm to 10.0 cm | 8.0 cm |
| Spathe durability | Spathes remain on plant for over a year | Spathes remain on plant for up to 8 months |

I claim:

1. A new and distinct cultivar of *anthurium* plant as shown and described herein.

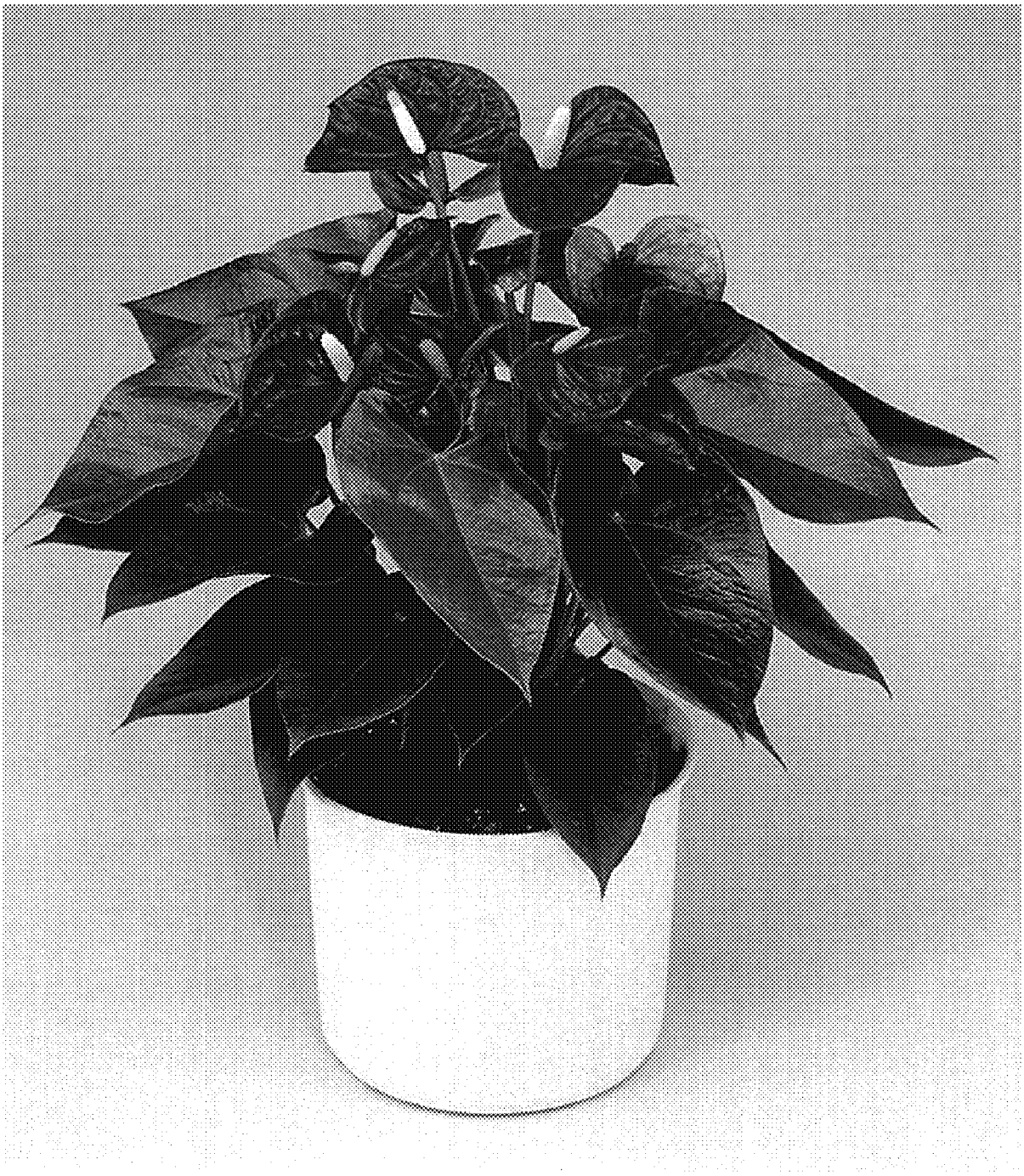

* * * * *